United States Patent
Lerner et al.

(10) Patent No.: US 10,655,124 B2
(45) Date of Patent: May 19, 2020

(54) PROXIMITY BASED METHODS FOR SELECTION OF BINDING PARTNERS

(71) Applicant: THE SCRIPPS RESEARCH INSTITUTE, La Jolla, CA (US)

(72) Inventors: Richard A. Lerner, La Jolla, CA (US); Hongkai Zhang, San Diego, CA (US); Jia Xie, San Diego, CA (US)

(73) Assignee: The Scripps Research Institute, La Jolla, CA (US)

(*) Notice: Subject to any disclaimer, the term of this patent is extended or adjusted under 35 U.S.C. 154(b) by 379 days.

(21) Appl. No.: 15/520,544

(22) PCT Filed: Oct. 16, 2015

(86) PCT No.: PCT/US2015/055941
§ 371 (c)(1),
(2) Date: Apr. 20, 2017

(87) PCT Pub. No.: WO2016/064673
PCT Pub. Date: Apr. 28, 2016

(65) Prior Publication Data
US 2018/0119133 A1    May 3, 2018

Related U.S. Application Data

(60) Provisional application No. 62/066,105, filed on Oct. 20, 2014.

(51) Int. Cl.
| | |
|---|---|
| *C12N 5/10* | (2006.01) |
| *G01N 33/566* | (2006.01) |
| *G01N 33/542* | (2006.01) |
| *C12N 15/10* | (2006.01) |

(52) U.S. Cl.
CPC ..... *C12N 15/1037* (2013.01); *C12N 15/1055* (2013.01); *C12N 15/1086* (2013.01); *G01N 33/542* (2013.01); *G01N 33/566* (2013.01); *G01N 2333/726* (2013.01)

(58) Field of Classification Search
CPC .................................................. C12N 15/1055
USPC ....................................................... 506/18, 10
See application file for complete search history.

(56) References Cited

U.S. PATENT DOCUMENTS

| | | | | |
|---|---|---|---|---|
| 2003/0078737 A1* | 4/2003 | Keys | .................. | G01N 21/6428 702/19 |
| 2005/0084864 A1* | 4/2005 | Rossner | ............. | C12N 15/1055 506/10 |
| 2009/0081639 A1* | 3/2009 | Hill | .................. | G01N 33/57407 435/5 |
| 2009/0252729 A1* | 10/2009 | Farrington | ......... | C07K 16/2875 424/135.1 |
| 2010/0203112 A1* | 8/2010 | Oh | ....................... | A61K 9/1272 424/450 |

(Continued)

FOREIGN PATENT DOCUMENTS

WO    WO-2013022739 A1 *  2/2013    ........... G01N 33/566

*Primary Examiner* — Karla A Dines
(74) *Attorney, Agent, or Firm* — Hugh Wang; Thomas Fitting

(57) ABSTRACT

The invention provides methods for identifying binding partners (e.g., peptide ligands) that binds to a target protein (e.g., a cellular receptor). The methods entail co-localized expression of the target protein and candidate binding partners, and selection of binding partners based on their proximity in the plasma membrane.

22 Claims, 4 Drawing Sheets

Specification includes a Sequence Listing.

Before Interaction

After Interaction (56) References Cited

U.S. PATENT DOCUMENTS

2014/0308675 A1* 10/2014 Mizota ............... G01N 33/5017
435/6.13
2019/0032043 A1* 1/2019 Daugherty ............... C12Q 1/37

* cited by examiner

SEQUENCE LISTING

```
<160> NUMBER OF SEQ ID NOS: 7

<210> SEQ ID NO 1
<211> LENGTH: 5
<212> TYPE: PRT
<213> ORGANISM: Artificial sequence
<220> FEATURE:
<223> OTHER INFORMATION: Synthetic sequence

<400> SEQUENCE: 1

Gly Gly Gly Gly Ser
1               5

<210> SEQ ID NO 2
<211> LENGTH: 7
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 2

Glu Xaa Xaa Tyr Xaa Gln Gly
1               5

<210> SEQ ID NO 3
<211> LENGTH: 7
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 3

Glu Xaa Xaa Tyr Xaa Gln Ser
1               5

<210> SEQ ID NO 4
<211> LENGTH: 7
<212> TYPE: PRT
<213> ORGANISM: Artificial sequence
```

```
<220> FEATURE:
<223> OTHER INFORMATION: Synthetic sequence

<400> SEQUENCE: 4

Glu Asn Leu Tyr Phe Gln Ser
1               5

<210> SEQ ID NO 5
<211> LENGTH: 7
<212> TYPE: PRT
<213> ORGANISM: Artificial sequence
<220> FEATURE:
<223> OTHER INFORMATION: Synthetic sequence

<400> SEQUENCE: 5

Glu Asn Phe Tyr Phe Gln Ser
1               5

<210> SEQ ID NO 6
<211> LENGTH: 7
<212> TYPE: PRT
<213> ORGANISM: Artificial sequence
<220> FEATURE:
<223> OTHER INFORMATION: Synthetic sequence

<400> SEQUENCE: 6

Glu Asn Leu Tyr Tyr Gln Ser
1               5

<210> SEQ ID NO 7
<211> LENGTH: 7
<212> TYPE: PRT
<213> ORGANISM: Artificial sequence
<220> FEATURE:
<223> OTHER INFORMATION: Synthetic sequence

<400> SEQUENCE: 7

Glu Asn Leu Phe Phe Gln Ser
1               5
```

PROXIMITY BASED METHODS FOR SELECTION OF BINDING PARTNERS

CROSS-REFERENCE TO RELATED APPLICATIONS

The subject patent application claims the benefit of priority to U.S. Provisional Patent Application No. 62/066,105 (filed Oct. 20, 2014). The full disclosure of the priority application is incorporated herein by reference in its entirety and for all purposes.

BACKGROUND OF THE INVENTION

Intracellular combinatorial libraries offer great promise for generation of novel agonists and other molecules that perturb cellular physiology. However, there is a need for a general-purpose readout mechanism that is quantitative over a large dynamic range. For example, current selection methods for identifying agonists in solution generally depend on their interaction with receptors to change their physical state so that they activate an intracellular signal transduction domain that is linked to a pejorative reporter system. Thus, each reporter system requires a separate construct whose nature depends on specific information about the cell and molecular biology of the system in question. Such a selection scheme cannot lead to systems that can report on binding events, especially when the mechanism of signal transduction is not known.

There is a need in the art for more dynamic and universal methods for selecting ligands based on binding events. The present invention addresses this and other unmet needs in the art.

SUMMARY OF THE INVENTION

The invention provides methods for identifying a binding partner that binds to a target polypeptide in a natural cellular milieu. In some methods, the target polypeptide is co-expressed in a cell with a combinatorial library of candidate binding partners using a lentiviral vector. In some methods, the candidate binding partners contain an enzyme that cleaves a signaling molecule that is fused to the target polypeptide, allowing signaling to a synthetic reporter system in a cell.

In some embodiments, methods of the invention entail (a) generating a first construct expressing a first fusion molecule comprising the target polypeptide containing a first transmembrane domain (TM), and a second construct expressing a combinatorial library of second fusion molecules each comprising a candidate binding partner linked to a second transmembrane domain (TM), wherein one of the fusion molecules further comprises an enzyme, and the other fusion molecule further comprises a substrate sequence of the enzyme and an activator of an artificial signaling pathway, (b) expressing the first construct and the second construct in a host cell to generate a population of cells, wherein each cell has the first fusion molecule and a second fusion molecule co-localized to the plasma membrane, (c) selecting a cell from the population of cells in which the artificial signaling pathway is activated, and (d) identifying the second fusion molecule in the selected cell. The identified second fusion molecule from the selected cell enables one to reveal a binding partner of the target polypeptide.

In some of these methods, the first transmembrane domain (TM) is a native domain of the target polypeptide. In some methods, the first transmembrane domain (TM) is recombinantly fused to the target polypeptide. In some methods, the enzyme is linked at its N-terminus to the second transmembrane domain, and the substrate sequence is linked at its N-terminus to the first transmembrane domain and at its C-terminus to the activator. In some methods, cleavage of the substrate sequence by the enzyme results in release of the activator from the second fusion molecule. In some methods, the target polypeptide is a cellular receptor, and the binding partner is a ligand of the receptor. In some of these methods, the cellular receptor is a cell surface receptor, and the second transmembrane domain is a PDGFR transmembrane domain. Some of these methods are directed to G-protein coupled receptors (GPCRs). Some of these methods are specifically directed to TpoR or GLP1R.

Some methods of the invention employ an enzyme that is a protease. In some of these methods, the substrate sequence contains a cleavage site of the protease. In some of these methods, the employed protease is TEV protease. In some of these methods, the employed substrate sequence contains ENLYFQS (SEQ ID NO:4) (TEV 1), ENFYFQS (SEQ ID NO:5) (TEV 2), ENLYYQS (SEQ ID NO:6) (TEV 3), or ENLFFQS (SEQ ID NO:7) (TEV 4). Some methods of the invention employ a host cell that is the HEK293 or the HEK293T cell. In some methods, the host cell stably expresses the first fusion molecule. In some of these methods, the second fusion molecule is expressed in the host cell via a lentiviral vector.

In some methods of the invention, the employed candidate binding partner is a peptide or an antibody. In some methods, the candidate binding partner is linked to the second transmembrane domain via a linker sequence. In some of these methods, the linker sequence can contain 3, 5, 6, 8, 10, or more tandem repeats of GGGGS (SEQ ID NO:1).

In some methods of the invention, the activator is a transcription factor, and the artificial signaling pathway is expression of a reporter gene under the control of a transcription regulatory sequence recognized by the transcription factor. In some of these methods, the reporter gene is introduced into the host cell via a lentiviral vector. In some methods, the reporter gene is introduced into the host cell prior to expression of the fusion molecules. In some methods, the transcription factor is GLA4-V16, and the transcription regulatory sequence contains GAL4 UAS and the adenovirus late promoter. In some methods, the employed reporter gene is luciferase luc2P gene or tdTomato reporter gene.

A further understanding of the nature and advantages of the present invention may be realized by reference to the remaining portions of the specification and claims.

DESCRIPTION OF THE DRAWINGS

FIG. 1. Schematic of the proximity based method for monitoring receptor-ligand interaction. (A) A membrane protein is coupled to a specific signal transduction pathway such that expression of the reporter gene is activated once the membrane protein is stimulated by a soluble or membrane tethered agonist. (B) The proximity based selection system consists of two membrane-tethered proteins. The first is a large library of membrane tethered potential ligands that are coupled to the protease TEV on their intracellular side. Secondly, a membrane tethered receptor protein has a TEV cleavage site and an artificial transcription factor appended to its intra-cellular side. Interaction of a co-located receptor protein and ligand approximates the TEV and TEV recognition site which greatly facilitates catalytic release of the transcription factor. The released transcription factor enters the cell nucleus and expression of the reporter gene is activated.

FIG. 2. Proximity based identification of Thrombopoietin receptor (TpoR) activation. Stable cell lines harboring the luciferase reporter gene under control of UAS and TpoR-TEV cleavage site-transcription factor were established. Cells were transduced with lentivirus encoding Thrombopoietin (TPO) or the TpoR binding antibodies 3D9 or 14F12. Genes encoding different linkers including 3, 5, 6, 8, or 10 copies of (GGGGS) (SEQ ID NO:1) or a human IgG1 Fc were placed between the ligand and PDGFR transmembrane domain. Luciferase activities were measured 2 days post infection. The cell line harboring GLP1R-TEV cleavage site-Transcription factor was used as negative cell control. The reaction was controlled by measuring the luminescence signals from control lentivirus carrying irrelevant antibodies with the same linker type and length.

FIG. 3A. Proximity based reaction for glucagon-like peptide 1 receptor (GLP1R). A Full length GLP1R (1-463) and a truncated GLP1R (1-426) were coupled to a TEV cleavage site and the transcription factor at the C-terminus. Stable cell lines harboring a luciferase reporter gene under control of UAS and different GLP1R constructs were established. Cells were transduced with lentivirus encoding the GLP1R natural ligand, Exendin-4, as a positive control or irrelevant antibodies as a negative control. Luciferase activities were measured 1-3 days post infection. The luminescence signals of infected cells were divided by the signals of corresponding uninfected cells to give the signal-to-noise ratio (S/N).

FIG. 3B. Enhancing the signal-to-noise ratio by varying the TEV cleavage site. Four TEV cleavage sites that are cleaved with varying efficiency were used for the GLP1R (1-426) constructions. Stable Cell lines containing the GLP1R constructions containing different TEV substrate sequences were transduced with lentivirus encoding the GLP1R natural ligand, Exendin-4, as the potentially positive construct, or Vc1.1 or irrelevant antibodies as negative controls. Luciferase activities were measured 1-3 days post infection. The luminescence signals of infected cells were divided by the signals of corresponding uninfected cells.

FIG. 4. Fluorescence proteins as reporter genes for the proximity based method. Stable cell lines containing the tdTomato reporter gene under control of UAS and GLP1R constructions with different TEV cleavage sites were studied. The cells were transduced with lentivirus containing Exendin-4 as a positive construct or irrelevant antibodies as negative controls. Selective expression of fluorescence protein was observed 2 days post infection.

DETAILED DESCRIPTION OF THE INVENTION

I. Overview

The present invention provides methods for identifying binding partners of target proteins or polypeptides. The target protein can be any protein or polypeptide that can bind to another polypeptide or peptide molecule, e.g., cell surface receptors, nuclear receptors and other ligand binding proteins. The methods rely on co-localized expression of the target protein (e.g., a cellular receptor) and candidate binding partners (e.g., candidate polypeptide ligands) and a proximity based selection format. The invention is predicated in part on the generation by the present inventors of a general system for identifying ligands of cellular receptors. The system takes advantage the chemical rate acceleration caused by proximity effects, approximation of a ligand and its receptor in space. The system uses an artificial signal transduction pathway and is, thus, agnostic to the exact chemical nature of the receptor-ligand system or the mechanism of its signal transduction. This method allows for autocrine selection of molecules from large libraries that interact with receptors when they are in their natural milieu. As detailed herein, the present invention provides a new and universal method to detect ligand-receptor binding activities. This is especially important in situations where the downstream signal transduction mechanism is unknown.

Proximity effects, manifest as effective molarities, regulate much of the biology of the cell. Such proximity effects can be achieved by compartmentalization, adherence to scaffolding molecules, or sequestration in enzyme active sites. Effective molarities can be as large as hundreds to $10^{10}$ molar. By choosing an appropriate enzyme-substrate system, an optimal reaction difficulty, and optimized linker lengths, the present invention allows one to generate a robust and general system that can be used to construct a reporter system for most membrane receptors and other binding proteins. Unlike selection methods presently known in the art, proximity-based reporter systems of the invention rely only on whether two molecules interacted and would be independent of the particular downstream requirements of the natural pathways. Instead, the system is linked to a universal reporting system whose chemistry would be favored relative to competing reactions because of proximity effects. Thus, in the context of a complicated system such as a cell, induced effective molarity becomes a specificity parameter to favor a given interaction.

As detailed herein, the methods of the invention employ intracellular combinatorial libraries of candidate binding partners and an expression system where the candidate binding partner and a protein of interest (e.g., a target receptor) are co-localized in cellular compartments (e.g., plasma membrane). The intra-cellular combinatorial libraries can express as many as $1.0 \times 10^8$ different antibodies or peptides in cells that also express the protein of interest. The expression system allows the interacting molecules to sequester and reach a higher effective molarity than might be achieved when they interact in bulk solution. Additionally, an enzyme-substrate reporting system is utilized which can take advantage of this molecular interaction in the plasma membrane and report on its occurrence. The enzyme-substrate system is constructed in a way that would be generalizable to any molecular interactions in the cellular compartments.

A further understanding of the nature and advantages of the present invention may be realized by reference to the remaining portions of the specification and claims.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press (1st ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al.

(Eds.), John Wiley & Sons (3$^{rd}$ ed., 2002); *Dictionary of Chemistry*, Hunt (Ed.), Routledge (1$^{st}$ ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology* (*Oxford Paperback Reference*), Martin and Hine (Eds.), Oxford University Press (4$^{th}$ ed., 2000). In addition, the following definitions are provided to assist the reader in the practice of the invention.

Unless defined otherwise, all technical and scientific terms used herein have the same meaning as commonly understood by those of ordinary skill in the art to which this invention pertains. The following references provide one of skill with a general definition of many of the terms used in this invention: Oxford Dictionary of Biochemistry and Molecular Biology, Smith et al. (eds.), Oxford University Press (revised ed., 2000); Dictionary of Microbiology and Molecular Biology, Singleton et al. (Eds.), John Wiley & Sons (3PrdP ed., 2002); and A Dictionary of Biology (*Oxford Paperback Reference*), Martin and Hine (Eds.), Oxford University Press (4PthP ed., 2000). In addition, the following definitions are provided to assist the reader in the practice of the invention.

The singular terms "a," "an," and "the" include plural referents unless the context clearly indicates otherwise. Similarly, the word "or" is intended to include "and" unless the context clearly indicates otherwise.

As used herein, the term "amino acid" of a peptide refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

The term "contacting" has its normal meaning and refers to combining two or more agents (e.g., polypeptides or small organic molecules), combining agents and cells, or combining two populations of different cells. Contacting can occur in vitro, e.g., mixing two polypeptides or mixing a population of antibodies with a population of cells in a test tube or growth medium. Contacting can also occur in a cell or in situ, e.g., contacting two polypeptides in a cell by coexpression in the cell of recombinant polynucleotides encoding the two polypeptides, or in a cell lysate.

For polypeptide sequences, "conservatively modified variants" refer to a variant which has conservative amino acid substitutions, amino acid residues replaced with other amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The term "engineered cell" or "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

Exendin-4 is a 39 amino acid agonist of the glucagon-like peptide 1 (GLP-1) receptor. Exendin-4 is present in the saliva of the Gila monster, *Heloderma suspectum*. Exendin-4 has a significantly longer half-life than GLP-1.

A "fusion" protein or polypeptide refers to a polypeptide comprised of at least two polypeptides and a linking sequence or a linkage to operatively link the two polypeptides into one continuous polypeptide. The two polypeptides linked in a fusion polypeptide are typically derived from two independent sources, and therefore a fusion polypeptide comprises two linked polypeptides not normally found linked in nature.

"Heterologous", when used with reference to two polypeptides, indicates that the two are not found in the same cell or microorganism in nature. Allelic variations or naturally-occurring mutational events do not give rise to a heterologous biomolecule or sequence as defined herein. A "heterologous" region of a vector construct is an identifiable segment of polynucleotide within a larger polynucleotide molecule that is not found in association with the larger molecule in nature. Thus, when the heterologous region encodes a mammalian gene, the gene will usually be flanked by polynucleotide that does not flank the mammalian genomic polynucleotide in the genome of the source organism.

The term "isolated" means a polypeptide or protein is removed from its natural surroundings. However, some of the components found with it may continue to be with an "isolated" protein. Thus, an "isolated polypeptide" is not as it appears in nature but may be substantially less than 100% pure protein.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

Methods of alignment of sequences for comparison are well known in the art. Optimal alignment of sequences for comparison can be conducted, e.g., by the local homology algorithm of Smith and Waterman, Adv. Appl. Math. 2:482c, 1970; by the homology alignment algorithm of Needleman and Wunsch, J. Mol. Biol. 48:443, 1970; by the search for similarity method of Pearson and Lipman, Proc. Nat'l. Acad. Sci. USA 85:2444, 1988; by computerized implementations of these algorithms (GAP, BESTFIT, FASTA, and TFASTA in the Wisconsin Genetics Software Package, Genetics Computer Group, Madison, Wis.); or by manual alignment and visual inspection (see, e.g., Brent et al., *Current Protocols in Molecular Biology*, John Wiley & Sons, Inc. (ringbou ed., 2003)). Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

A "ligand" is a molecule that is recognized by a particular antigen, receptor or target molecule. Examples of ligands that can be employed in the practice of the present invention may include, but are not restricted to, agonists and antagonists for cell membrane receptors, toxins and venoms, viral epitopes, hormones, hormone receptors, polypeptides, peptides, enzymes, enzyme substrates, cofactors, drugs (e.g. opiates, steroids, etc.), lectins, sugars, polynucleotides, nucleic acids, oligosaccharides, proteins, and monoclonal antibodies.

"Linkage" refers to means of operably or functionally connecting two biomolecules (e.g., polypeptides or polynucleotides encoding two polypeptides), including, without limitation, recombinant fusion, covalent bonding, disulfide bonding, ionic bonding, hydrogen bonding, and electrostatic bonding. "Fused" refers to linkage by covalent bonding. A "linker" or "spacer" refers to a molecule or group of molecules that connects two biomolecules, and serves to place the two molecules in a preferred configuration with minimal steric hindrance.

The term "operably linked" when referring to a nucleic acid, refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

Unless otherwise specified, the terms "polypeptide" and "peptide" are used interchangeably herein to refer to a polymer of amino acid residues. They encompass both short oligopeptides (e.g., peptides with less than about 25 residues) and longer polypeptide molecules (e.g., polymers of more than about 25 or 30 amino acid residues). Typically, the candidate peptide or polypeptide ligands used in the invention can comprise from about 4 amino acid residues to about 350 or more amino acid residues in length. In some embodiments, the peptides or polypeptides comprise from about 6 amino acid residues to about 60 amino acid residues in length. In some other embodiments, they can comprise from about 8 amino acid residues to about 40 amino acid residues in length. The peptides or polypeptides can include naturally occurring amino acid polymers and non-naturally occurring amino acid polymer, as well as amino acid polymers in which one or more amino acid residue is an artificial chemical mimetic of a corresponding naturally occurring amino acid. Unless otherwise indicated, a particular polypeptide sequence also implicitly encompasses conservatively modified variants thereof.

As used herein, the term "peptide mimetic" or "peptidomimetic" refers to a derivative compound of a reference peptide that biologically mimics the peptide's functions. Typically, the peptidomimetic derivative has at least 50%, at least 75% or at least 90% of the biological function of the reference polypeptide.

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

Unless otherwise noted, the term "receptor" broadly refers to a molecule that has an affinity for a given ligand. Receptors may-be naturally-occurring or manmade molecules. Also, they can be employed in their unaltered state or as aggregates with other species. Receptors may be attached, covalently or noncovalently, to a binding member, either directly or via a specific binding substance. A typical example of receptors which can be employed in the practice of the invention is cell surface signaling receptor.

The phrase "signal transduction pathway" or "signaling activities" (e.g., the GLP-1R mediated signaling) refers to at least one biochemical reaction, but more commonly a series of biochemical reactions, which result from interaction of a cell with a stimulatory compound or agent. Thus, the interaction of a stimulatory compound with a cell generates a "signal" that is transmitted through the signal transduction pathway, ultimately resulting in a cellular response.

As used herein, the term "variant" refers to a molecule (e.g., a peptide or polypeptide) that contains a sequence that is substantially identical to the sequence of a reference molecule. For example, the reference molecule can be an enzymatic polypeptide disclosed herein or a fusion thereof.

The reference molecule can also be a polynucleotide encoding the polypeptide. In some embodiments, the variant can share at least 50%, at least 70%, at least 80%, at least 90%, at least 95% or more sequence identity with the reference molecule. In some other embodiments, the variant differs from the reference molecule by having one or more conservative amino acid substitutions. In some other embodiments, a variant of a reference molecule is a conservatively modified variant, e.g., a variant which has altered amino acid sequences (e.g., with one or more conservative amino acid substitutions) but substantially retains the biological activity of the reference molecule. Conservative amino acid substitutions are well known to one skilled in the art.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors").

III. Expression System for Proximity Based Selection

Methods of the invention utilize an expression system that allows an expressed target protein (e.g., a cellular receptor) and a library of candidate binding partners (e.g., candidate polypeptide ligands) anchored and co-localized in a cellular compartment, e.g., the plasma membrane. The candidate binding partners are expressed via an intracellular combinatorial library. Interaction of the target protein and the binding partner will activate an enzyme-substrate system that reports on the occurrence of the molecular interaction in the cellular compartment (e.g., plasma membrane). The target protein and the binding partner are expressed in a manner so that each is fused to or carries only one component of the enzyme-substrate reporter system. Using a cell surface receptor and a peptide ligand as an example, the system only functions when the ligand and receptor interact to bring the reactants into proximity. When the interaction between the receptor and its ligand cause them to approximate, a proteolytic reaction releases an activator or effector molecule which can bring about a detectable response in the host cell. For example, the activator can be a peptide or polypeptide transcription factor that enters the nucleus and binds to a promoter in the nucleus to activate a reporter gene. There are many advantages derived from this expression system and the resulting selection format. For example, the system allows molecular interactions of large numbers of potential agonists to be determined in the physiologically relevant milieu of the intact living cell. In addition, the system enables one to search for ligands of receptors where the mechanism of signal transduction is unknown or the ligand itself is unknown.

For co-localized expression of the candidate binding partners (e.g., polypeptide ligands) and the target protein (e.g., a cellular receptor) to plasma membrane, the binding partner can be fused to a trans-membrane protein domain and expressed from a first expression construct. The target protein is expressed as a fusion from a second expression construct. In some embodiments, the target protein is a cell surface receptor that contains one or more native transmembrane domains (TMs), e.g., the extracellular domain along with the native TM of a cell surface receptor. In some other embodiments wherein the target protein lacks a native TM (e.g., a nuclear receptor or other ligand binding protein), it can be expressed as a fusion with a heterologous trans-membrane protein domain. In some embodiments, a linker sequence is used in the expression constructs that connects the components of the fusion polypeptide, e.g., connecting the candidate ligand (e.g., an antibody or a peptide) to the trans-membrane protein domain. For example, most of the membrane-tethered toxins generated so far contain a stretch of 20 alternating glycine and asparagine residues. This linker sequence can be used in the expression constructs of the invention. Such a linker preceding the membrane tether can provide the rotational flexibility and distance necessary for the peptide toxin to bind to its cognate ion channel. In various embodiments, linkers of various lengths can be used and optimized for expressing the fusion constructs.

To exemplify the selection scheme with a receptor and a peptide ligand, the candidate ligand and the receptor are expressed in a manner so that each is fused to or carries only one component of the enzyme-substrate reporter system. Thus, as exemplified herein, the ligand-TM fusion construct can additionally express the enzyme (or its substrate), and the receptor construct can additionally express the substrate sequence (or the enzyme). In various embodiments, the substrate peptide sequence is further linked to an effector or activator sequence (e.g., a transcription factor). Upon binding of the ligand to the receptor, enzymatic cleavage of the substrate sequence will result in release of the effector molecule. The released effector molecule can then activate a detectable signaling pathway in the cell, providing an indication that the ligand-receptor binding event has taken place.

The enzyme-substrate reporter suitable for the invention is not limited to any particular enzyme-substrate system; any of a number of well-known enzyme and polypeptide substrate pairs can be employed in the practice of the present invention. As exemplified herein, one example of the enzyme-substrate system is TEV protease and a specific peptide cleavage site of the enzyme. TEV protease is a well-known and highly sequence-specific cysteine protease from Tobacco Etch Virus (TEV). It is a member of the PA class of chymotrypsin-like proteases. Due to its high sequence specificity it is frequently used for the controlled cleavage of fusion proteins in vitro and in vivo. In the practice of the present invention, the wildtype TEV protease, any variants (e.g., conservatively modified variants) or enzymatic fragments of the wildtype enzyme may be used. Sequences and vectors expressing TEV protease and variants are routinely used in the art, and are readily available in the literature or commercial suppliers, e.g., Kapust et al Prot. Expr. Purif., 19:312-8, 2000; Kapust et al., Prot. Eng., 14: 993-1000, 2001; Chen et al., Prot. Sci. 19:2379-88, 2010; and Addgene (Cambridge, Mass.). The corresponding cleavage site sequences of TEV protease have also been well characterized and used in the art. Examples of suitable substrate sequences for TEV protease include, e.g., ENLYFQS (SEQ ID NO:4) (TEV1), ENFYFQS (SEQ ID NO:5) (TEV 2), ENLYYQS (SEQ ID NO:6) (TEV 3) and ENLFFQS (SEQ ID NO:7). In some embodiments, the TEV protease substrate sequence used in the constructs of the invention is ENFYFQS (SEQ ID NO:5) (TEV 2).

Similarly, any reporter gene well known in the art can be employed in the practice of the present invention. It can be any gene or polynucleotide encoding a protein whose expression by a cell can be detected and/or quantified. Thus, a measurement of the level of expression of the reporter is indicative of the level of activation of the promoter element that directs expression of the reporter gene. Examples of genes useful as reporter genes include, e.g., genes that encode a metabolic enzyme, an antibiotic resistance factor, a luminescent protein, or a fluorescent protein. Such reporter genes are well known in the art and particular examples are described in Wood (1995) *Curr. Opin. Biotechnol.* 6(1): 50-58. In some constructs of the invention, the reporter gene encodes a luciferase. In some other embodiments, the reporter gene encodes a metabolic enzyme such as β-galactosidase. In some embodiments, the reporter gene can be a gene that complements an auxotrophic mutation in a host cell and allows growth of cells that express the gene on selective media.

Construction of the expression vectors and reporter cells for practicing methods of the invention can be readily carried out in accordance with routinely practiced methods of molecular biology. Some specific protocols for performing the required steps of the invention are also exemplified herein. For example, as detailed herein, expression vectors encoding a ligand-TM-enzyme fusion can be generated by fusing the candidate ligands to the N-terminus of the PDGFR transmembrane domain (amino acids 514-561) while the enzyme (e.g., TEV protease) is fused to the C-terminus of the transmembrane domain. To allow rotational flexibility, a linker sequence can be inserted between the ligand sequence and the transmembrane domain. One linker sequence as exemplified herein contains one or more (e.g., 1, 2, 3, 4, 5, 6, 7, 8, 9, 10, 15, 20 or more) tandem repeats of GGGGS (SEQ ID NO:1). In some embodiments, the linker comprises 8, 10 or more tandem repeats of GGGGS (SEQ ID NO:1). The ligand-TM-enzyme fusion can be cloned into a lentiviral vector (e.g., the pLV2 vector exemplified herein) to produce viral particles for transfecting the host cell. For the receptor-substrate-effector molecule fusion, an exemplary effector molecule can be the fusion of a Gal4 DNA-binding domain to the Herpes simplex virus VP16 C terminal activation domain. This results in an artificial transcription factor (GAL4-VP16) that is orthogonal to all mammalian cells. The coding region of the target receptor (e.g., TpoR or GLP1R) is fused at its C-terminus to the substrate sequence or cleavage site of the enzyme (e.g., the TEV protease cleavage site) and the GAL4-VP16 transcription factor. This fusion sequence can then be cloned into an appropriate expression vector (e.g., the pcDNA5 vector).

Various expression vectors can be used in the invention. For example, lentiviral vectors are suitable for introducing into and expressing in the host cell the combinatorial library of candidate binding partners. Lentiviral vectors are retroviral vectors that are able to transduce or infect both dividing and non-dividing cells and typically produce high viral titers. Examples of lentiviral based vectors suitable for the invention include, e.g., the pLV2 lentiviral vector exemplified herein. Other lentiviral vectors that may be employed and modified for practicing the invention include, e.g., pLVX-Puro, pLVX-IRES-Neo, pLVX-IRES-Hyg, and pLVX-IRES-Puro. The various lentiviral vectors with cloned candidate ligand sequences can be introduced into an appropriate host cell for expressing the candidate ligand library. For example, the HEK293 cell line, the HEK293T cell line, and the TF-1 cell line are all suitable for the invention. Many other packaging cell lines well known in the art (e.g., Lenti-X 293T cell line) may also be employed for expressing the combinatorial library in the invention. In addition to lentiviral based vectors and host cells, other retroviral based vectors and expression systems may also be employed in the practice of the methods of the invention. These include MMLV based vectors pQCXIN, pQCXIQ and pQCXIH, and compatible producer cell lines such as HEK 293 based packaging cell lines GP2-293, EcoPack 2-293 and AmphoPack 293, as well as NIH/3T3-based packaging cell line RetroPack PT67.

To identify candidate ligands that can bind to the receptor, the host cell can also contain a detectable reporter gene that can be activated by the effector molecule to allow detection of the occurrence of a binding event. For example, when the chosen effector molecule is the GAL4-VP16 transcription factor, a UAS-reporter reporter gene vector can be introduced into the host cell. As exemplified herein, the reporter gene vector contains a transcription control sequence (e.g., several repeats of GAL4 UAS and the adenovirus late promoter) that is recognized by the GAL4-VP16 transcription factor and activates expression of an operably linked sequence. The operably linked sequence typically encodes an easily detectable signal. For example, the transcription control sequence in the reporter gene vector can drive the transcription of the luciferase luc2P or tdTomato reporter gene in response to binding of GAL4-VP16 transcription factor. As exemplified herein, stable host cells or cell lines harboring the reporter gene can be easily generated by transfecting the host cell (e.g., HEK293 cells) with the reporter gene construct (e.g., the UAS-reporter gene vector).

The invention has exemplified detection of co-localized expression and binding of ligands to TpoR and GLP-1R receptors. The generic selection scheme described herein can be broadly applied in identifying ligands of any cellular receptors. These include any cell surface receptors (e.g., GPCRs or enzyme linked receptors) which typically contain their own transmembrane domains, e.g., GPCRs and enzyme-linked receptor. In addition to surface receptors with transmembrane domains, other cellular receptors or ligand-binding proteins can also be examined in the selection system of the invention to identify their ligands or binding partners, including, e.g., cytoplasmic receptors or nuclear receptors. For receptors or ligand-binding proteins lacking native transmembrane domains, they can be recombinantly fused to a heterologous transmembrane domain (e.g., PDGFR TM) before being used in the selection methods of the invention. In various embodiments, the selection system can be used to identify novel ligands or modulators (agonists or antagonists) of receptors of which no ligands have been identified (orphan receptors). For receptors having a known ligand, the identification of novel agonists or antagonists may be sought specifically for mimicking, enhancing or inhibiting the action of the ligand.

Some embodiments of the invention are directed to G-protein-coupled receptors (GPCRs). GPCRs constitute the largest family of cell surface receptor proteins. There are three major families of GPCRs, Gs-, Gi-, and Gq-coupled receptors. Upon activation, different GPCRs stimulate a number of signal transduction pathways. For example, Gs-coupled receptor increases while Gi-coupled receptor decreases cAMP production. Therefore, these two different GPCRs can activate or inhibit the cAMP-response element. On the other hand, Gq-coupled receptor increases intracellular calcium concentration and activates the multiple-response element. Based on sequence homology and functional similarity, GPCRs can be classified into Class A (Rhodopsin-like receptors), Class B (Secretin receptor family), Class C (Metabotropic glutamate/pheromone), Class D (Fungal mating pheromone receptors), Class E (Cyclic AMP receptors), and Class F (Frizzled/Smoothened receptors). Some embodiments of the invention are directed to enzyme-linked receptors. Enzyme-linked receptors encompass receptor tyrosine kinases; tyrosine kinase associated receptors; receptor-like tyrosine phosphatases; receptor serine/threonine kinases; receptor guanylyl cyclases, and histidine kinase associated receptors. Of these, receptor tyrosine kinases represent the largest population of enzyme-linked receptors. The majority of these molecules are receptors for growth factors and hormones like epidermal growth factor (EGF), platelet derived growth factor (PDGF), fibroblast growth factor (FGF), hepatocyte growth factor (HGF), insulin, nerve growth factor (NGF) etc.

Other than co-localization to plasma membrane, methods of the invention can also be used for selecting ligands co-localized with a receptor to other cellular compartments. Any situation where two proteins are selectively approximated will increase the effective molarity of their interaction. Thus, for example, methods of the invention can also be employed to monitor organelle-organelle interactions or generally follow protein trafficking by redirecting the reporter system.

IV. Plasma Membrane Localized Ligand Libraries

The invention provides combinatorial libraries of polypeptides or antibodies (e.g., single chain antibodies) which can be localized to plasma membrane upon being expressed in cells. The libraries can each contain at least $1\times10^4$, $1\times10^5$, $1\times10^6$, $1\times10^7$, $1\times10^8$, $1\times10^9$, $1\times10^{10}$ or more different polypeptide or antibody sequences. Typically, each member of the library contains a specific or randomized polypeptide or antibody sequence which is operably liked to a transmembrane domain. The transmembrane domain, e.g., a PDGFR transmembrane region as exemplified herein, allows the expressed peptides to be tethered to cell membrane. Other than PDGFR, many other transmembrane domains well known in the art, as well as variants (e.g., conservatively modified variants) of these known transmembrane protein domains, can also be employed in the construction of the ligand libraries of the invention. See, e.g., Remm et al., Genome Res. 10: 1679-1689, 2000; and Hubert et al., Cell Adh. Migr. 4: 313-324, 2010.

In some embodiments, the candidate ligands are a combinatorial library of polypeptide or peptide sequences. Any polypeptide or peptide (e.g., a randomized peptide) can be employed in the construction of the combinatory libraries of the invention. They can contain at least 4, 5, 6, 7, 8, 10, 15, 20, 25, 50, 100, 200, 300 or more amino acid residues in length. Conventional genetic engineering techniques are typically employed for expression of the library of polypeptides. To produce the recombinant polypeptide or peptide library of the invention, the polynucleotides encoding the peptide are inserted into a suitable expression system. Expression of the fusion peptides can employ numerous types of appropriate expression vectors known in the art, including, e.g., vectors containing bacterial, viral, yeast, fungal, insect or mammalian expression systems. As exemplified herein, a preferred expression system for producing the peptide or polypeptide libraries of the invention is lentiviral based. Methods for obtaining and using such expression vectors are well-known. For guidance in this and other molecular biology techniques used for generating and expressing the combinatorial libraries of the invention, see, e.g., Sambrook et al, Molecular Cloning, A Laboratory Manual, current edition, Cold Spring Harbor Laboratory, New York; Miller et al, Genetic Engineering, 8:277-298 (Plenum Press, current edition), Wu et al, Methods in Gene Biotechnology (CRC Press, New York, N.Y., current edition), Recombinant Gene Expression Protocols, in Methods in Molecular Biology, Vol. 62, (Tuan, ed., Humana Press, Totowa, N.J., current edition), and Current Protocols in Molecular Biology, (Ausubel et al., Eds.,) John Wiley & Sons, NY (current edition), and references cited therein. In an exemplified embodiment, the polynucleotide can be placed under the control of an appropriate promoter in an expression vector, e.g., EF1a promoter in a lentiviral vector as exemplified herein.

In some embodiments of the invention, the combinatorial library of ligands used is a library of antibodies. Any antibody sequences can be employed in the construction of the combinatory peptide libraries of the invention. In some embodiments, a single chain antibody library is typically used. Single chain antibody libraries can comprise the heavy or light chain of an antibody alone or the variable domain thereof. However, more typically, the members of single-chain antibody libraries are formed from a fusion of heavy and light chain variable domains separated by a peptide spacer within a single contiguous protein. See e.g., Ladner et al., WO 88/06630; McCafferty et al., WO 92/01047. The diversity of antibody libraries can arise from obtaining antibody-encoding sequences from a natural source, such as a nonclonal population of immunized or unimmunized B cells. Alternatively, or additionally, diversity can be introduced by artificial mutagenesis as well known in the art. In some embodiments, the antibody library expresses single chain variable region fragments (scFv). A specific scFv library suitable for use in the present invention is described in the art, e.g., Gao et al., Proc. Natl. Acad. Sci. 99:12612-6, 2012. Such an antibody library can be generated with and expressed from various vectors well known in the art. Preferably, the antibody library used in the invention is constructed via a lentiviral or retroviral based vector. Construction of such antibody library for expression inside a eukaryotic host cell can be performed in accordance with the techniques exemplified herein and other methods well known in the art.

Many techniques well known in the art can be readily employed to increase the diversity of the members of a library of candidate ligands. These include, e.g., combinatorial chain shuffling, humanization of antibody sequences, introduction of mutations, affinity maturation, use of mutator host cells, etc. These methods can all be employed in the practice of the methods described herein at the discretion of the artisan. See, e.g., Aujame et al., Hum. Antibod. 8: 155-168, 1997; Barbas et al., Proc. Natl. Acad. Sci. USA 88: 7978-82, 1991; Barbas et al., Proc. Natl. Acad. Sci. USA 91: 3809-13, 1994; Boder et al., Proc. Natl. Acad. Sci. USA 97: 10701-10705, 2000; Crameri et al., Nat. Med. 2: 100-102, 1996; Fisch et al., Proc. Natl. Acad. Sci. USA 93: 7761-7766, 1996; Glaser et al., J. Immunol. 149: 3903-3913, 1992; Eying et al., Immunotechnology, 2: 127-143, 1996; Kanppik et al., J. Mol. Biol., 296: 57-86, 2000; Low et al., J. Mol. Biol. 260: 359-368, 1996; Riechmann and Winter, Proc. Natl. Acad. Sci. USA, 97: 10068-10073, 2000; and Yang et al., J. Mol. Biol. 254: 392-403, 1995.

In some embodiments, the libraries of candidate ligands contain variants or mutants derived from a single candidate polypeptide or a starting framework polypeptide (e.g., a known polypeptide ligand of a cellular receptor). For example, a polynucleotide molecule encoding the candidate polypeptide may be altered at one or more selected codons. An alteration is defined as a substitution, deletion, or insertion of one or more nucleotides in the gene encoding the candidate polypeptide that results in a change in the amino acid sequence of the polypeptide. Preferably, the alterations will be by substitution of at least one amino acid with any other amino acid in one or more regions of the molecule. The alterations may be produced by a variety of methods known in the art. These methods include, but are not limited to, oligonucleotide-mediated mutagenesis (e.g., Zoller et al., Methods Enzymol. 154:329-50, 1987), cassette mutagenesis (e.g., Well et al. Gene 34:315, 1985), error-prone PCR (see, e.g., Saiki et al., Proc. Natl. Acad. Sci. USA. 86:6230-4, 1989; and Keohavong and Thilly, Proc. Natl. Acad. Sci. USA., 86:9253-7, 1989), and DNA shuffling (Stemmer, Nature 370:389-91, 1994; and Stemmer, Proc. Natl. Acad. Sci. 91:10747-51, 1994).

In some embodiments, the candidate ligands can be further conjugated to a fusion partner (e.g. another peptide or other moiety) that can be used to improve purification, to enhance expression of the peptide in a host cell, to aid in detection, to stabilize the peptide, etc. Examples of suitable fusion partners for the candidate peptide ligands of the invention include polyethylene glycol, PEGylation, or other chemicals. Among the many suitable peptide or polypeptide fusion partners are, e.g., .beta.-galactosidase, glutathione-S-transferase, a histidine tag, etc. In some embodiments, the candidate peptides or polypeptides of the invention can be provided with a detectable label.

In some embodiments, the candidate ligands can contain one or more naturally occurring amino acid derivatives of the twenty standard amino acids, for example, 4-hydroxy-proline, 5-hydroxylysine, 3-methylhistidine, homoserine, ornithine or carboxyglutamate, and can include amino acids that are not linked by polypeptide bonds. Similarly, they can also be cyclic polypeptides and other conformationally constrained structures. Methods for modifying a polypeptide to generate analogs and derivatives are well known in the art, e.g., Roberts and Vellaccio, *The Peptides: Analysis, Synthesis, Biology*, Eds. Gross and Meinhofer, Vol. 5, p. 341, Academic Press, Inc., New York, N.Y. (1983); and *Burger's Medicinal Chemistry and Drug Discovery*, Ed. Manfred E. Wolff, Ch. 15, pp. 619-620, John Wiley & Sons Inc., New York, N.Y. (1995).

V. Selecting Ligands Via Proximity Based Assays

The invention provides methods for identifying one or more ligands of a target molecule (e.g., a target receptor) from a large intracellular combinatorial library of candidate ligands that can be expressed and localized to the plasma membrane of a population of host cells. In these methods, different candidate ligands from the library and the target molecule (e.g., a surface receptor) are co-localized to the plasma membrane of the host cells. The target molecule (e.g., receptor) and the candidate ligand are each fused to one component of an enzyme and a cognate peptide substrate or recognition sequence of the enzyme. When the co-localized ligand binds to the neighboring target molecule (e.g., receptor), an effector cell (e.g., transcription factor) fused to the substrate sequence is released as a result of an enzymatic reaction. The effector molecule can then lead to a detectable response upon activating an artificial cellular response or signaling pathway, e.g., a fluorescent response, a luminescent response or other signal.

The host cells for practicing methods of the invention can be any well known eukaryotic cells or cell lines suitable for harboring and expressing the target molecule, the candidate ligands, and the reporter construct described herein. In some embodiments, mammalian host cells are used to express the fusion molecules for proximity based ligand selection. For example, they can be either a hybridoma cell line or a mammalian cell line (e.g., HEK293 cells) harboring exogenous expression vectors as exemplified below. These include any normal mortal or abnormal immortal animal or human cell. In addition to the cell lines exemplified herein, a number of other suitable host cell lines capable of expressing the target molecule and the candidate ligand constructs of the invention are also known in the art. These include, e.g., the CHO cell lines, various COS cell lines, HeLa cells, myeloma cell lines, transformed B-cells and other hybridoma cell lines. The use of mammalian tissue cell culture to express polypeptides is discussed generally in, e.g., Winnacker, *From Genes to Clones*, VCH Publishers, N.Y., N.Y., 1987. Expression vectors for mammalian host cells can include expression control sequences, such as an origin of replication, a promoter, and an enhancer, and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, EF1α and human UbC promoters exemplified herein, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Expression of the candidate ligand construct and the target molecule (e.g., a receptor) construct for monitoring binding activities can be performed with routinely practiced techniques of molecular biology and the methods exemplified herein. Selection from the library of candidate ligands for ligands of a target receptor can also be performed with standard procedures well known in the art or the specific exemplifications described herein. Regardless of the ligands used, a library of expression vectors (e.g., lentiviral vectors) encoding the combinatorial library of polypeptide or antibody ligands can first be introduced into appropriate host cells (e.g., HEK293) to provide a library of ligand-encoding viruses. Upon co-transfecting the viruses into host cells along with a virus expressing a specific membrane bound target molecule (a receptor such as TpoR or GLP-1R), the library of ligand fusions will be expressed and become co-localized to the membrane with the receptor. In some embodiments, the target molecule-expressing vector and the reporter gene construct can be first introduced into the host cell. The ligand-expressing library can then be introduced into the host cell that stably expresses the target molecule (e.g., a surface receptor).

Depending on the specific effector molecule and reporter gene employed in the methods, various proximity based reaction assays can be used to detect binding of ligands to the target molecule. Using the GAL4-VP16 transcription factor and the GAL4 UAS transcription response element as an example, the host cell harboring both the UAS-reporter gene and the target receptor-cleavage site-transcription factor fusion can be first infected by lentiviruses carrying the library of candidate ligand-TM-TEV protease fusions. Cells are then cultured before measuring the reporter gene activity.

The invention can employ various methods for detecting and quantitating reporter expression that are commonly based on measuring the activity of the protein encoded by the reporter. A wide variety of appropriate detectable markers are known in the art, including fluorescent, radioactive, enzymatic or other ligands, such as avidin/biotin, which are capable of giving a detectable signal. In some embodiments, one can employ a fluorescent label or an enzyme tag, such as urease, alkaline phosphatase or peroxidase, instead of radioactive or other environmentally undesirable reagents. In the case of enzyme tags, colorimetric indicator substrates are known which can be employed to provide a means visible to the human eye or spectrophotometrically. As exemplified herein, the reporter gene can be a luciferase gene the expression of which can be readily detected via luciferase assays, or the tdTomato gene the expression of which can be observed by fluorescent microscopy. Other examples of reporter genes suitable for the invention include the beta-lactamase, and genes encoding GFP or other fluorescence proteins that can be visualized by fluorescence microscopy or detected using fluorescence activated cell sorting.

When the reporter gene encodes an enzyme, a substrate for the enzyme which is metabolized to produce a measurable product can be used. For example, the β-galactosidase substrate X-gal, which is cleaved by this enzyme to produce a blue reaction product, is frequently used to assay β-galactosidase reporter expression. (Miller J. ed. (1992) *A Short Course in Bacterial Genetics: A Laboratory Manual and Handbook for Escherichia Coli and Related Bacteria*, Cold Spring Harbor Laboratory, Cold Spring Harbor, N.Y. Alternatively, the β-galactosidase substrate o-nitrophyl-B-D-galactopyranoside (ONPG), which is metabolized by β-galactosidase to produce a compound with a yellow color. The quantity of enzyme is determined by measuring optical density of the colored compound spectrophotometrically or with an ELISA reader. The absorbance is read at 420 nm (Miller J. H. ed. (1972) *Experiments in Molecular Genetics*, Cold Spring Harbor Laboratory, Cold Spring Harbor, New York). Other commonly used reporter genes are the antibiotic resistance factor chloramphenicol acetyl transferase (CAT), the firefly luciferase gene (as shown in the Examples below), and the jellyfish green fluorescent protein (Valdivia and Falkow (1997) *Trends Microbiol.* 5(9):360-363; Naylor (1999) *Biochem. Pharmacol.* 58(5):749-757; Himes and Shannon (2000) *Methods Mol. Biol.* 130:165-174). In addition, a variety of alternative proteins can also be used as reporters based on their ability to be detected and quantitated. Assays to measure the expression levels of such genes are well developed and are commonly practiced by those of ordinary skill (Rosenthal (1987) *Methods Enzymology* 152: 704-720; Davey et al. (1995) *Methods Mol. Biol.* 49:143-148; and Bronstein et al. (1994) *Anal. Biochem.* 219(2):169-181).

EXAMPLES

The following examples are provided to further illustrate the invention but not to limit its scope. Other variants of the invention will be readily apparent to one of ordinary skill in the art and are encompassed by the appended claims.

Example 1. Materials and Methods

Cell Lines.

HEK293 (ATCC cat no. CRL-1573) or HEK293T (ATCC cat no. CRL-3216) cells were maintained in DMEM containing 10% (vol/vol) FBS, penicillin and streptomycin and transfected using Lipofectamine 2000 (Life technologies). Mammalian cell antibiotics Geneticin and Hygromycin were from Invivogen. Luciferase Assay Reagent was obtained from Promega (E1500).

Plasmid Construction. Lentiviral Vector Encoding Ligand-TM-TEV Protease.

The ligand was fused to the N terminus of the PDGFR trans-membrane domain (amino acids 514-561) while the TEV protease was fused to the C-terminus of the trans-membrane domain. Different numbers of GGGGS (SEQ ID NO:1) linker sequences were added between the ligand and trans-membrane domain. The ligand-trans-membrane-TEV was introduced into the lentiviral vector under control of the UBC (Ubiquitin C) promoter.

Receptor-TEV Cleavage Site-GAL4-VP16 Transcription Factor Vector.

The Gal4 DNA-binding domain was fused to the Herpes simplex virus VP16 C terminal activation domain to generate an artificial transcription factor that is orthogonal to mammalian cells. The coding region of TpoR or GLP1R was followed by the TEV protease cleavage site and the GAL4-VP16 transcription factor and cloned into pcDNA5 whose expression was under control of CMV promoter. The vector has a Gentamicin selection cassette, for the generation of stable cell lines.

Upstream Activator Sequence Reporter Gene Vector (UAS).

The UAS-reporter gene vector contains 9 repeats of GAL4 UAS and the adenovirus late promoter. This sequence drives the transcription of the luciferase luc2P or tdTomato reporter gene in response to binding of GAL4-VP16 transcription factor. The vector has a Hygromycin selection cassette, for the generation of stable cell lines.

Generation of Stable Reporter Cell Line.

Stable cell lines were generated by transfection HEK293 cells with UAS-reporter gene vector first using Lipofectamine. The transfected cells were selected in 200 ug/mL Hygromycin. After two weeks, the selected cells were harvested and transfected with the specific receptor-TEV cleavage site-GAL4-VP16 transcription factor vector. The cells were selected in 800 ug/mL Gentamicin and 100 ug/mL Hygromycin for two weeks.

Package of Lentivirus.

Virus was produced in HEK293T cells by co-transfection of lentiviral vectors with the pCMVD8.9 and pVSVg viral packaging vectors at ratio of 1:1:1. Supernatants containing virus were collected at 48 h post-transfection and filtered through a 0.22 um membrane filter unit (Millipore). The titer of lentivirus prep was determined using Lenti-X p24 ELISA (Clontech).

Proximity Based Reaction Assay.

The stable cell line harboring both the UAS-reporter gene and receptor-cleavage site-transcription factor was plated in a 96 well plate at 20000 cells per well. Cells were infected by lentivirus carrying the ligand-TM-TEV protease at MOI equal to 1. Cells were cultured for 24-72 h before measuring the reporter gene activity. Luciferase activity was determined by using a luciferase assay system (Promega) while expression of tdTomato was observed by fluorescent microscopy.

Example 2. System Constructions

Figure 1:
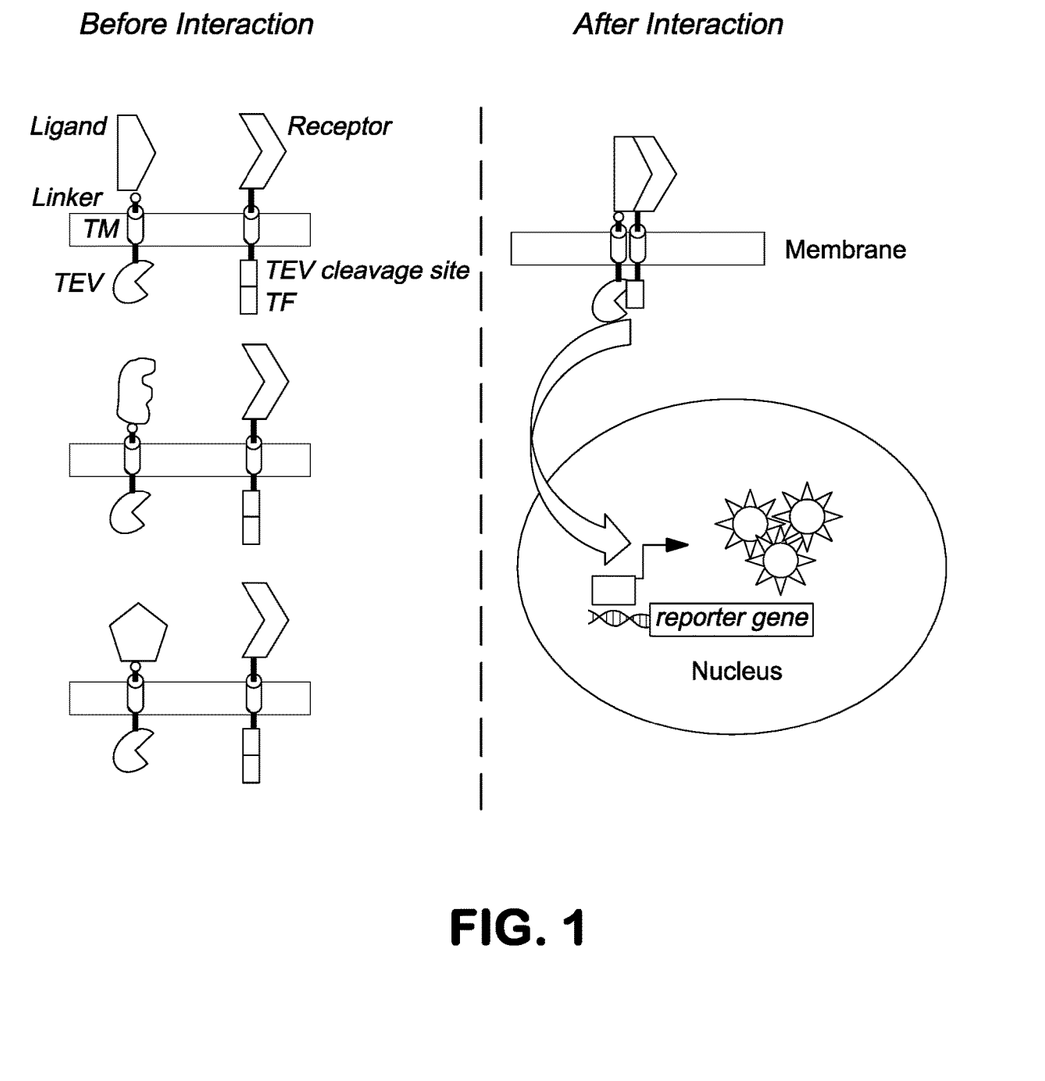

We constructed an enzyme-substrate system where the proteolytic reaction is inefficient so that at basal concentrations it proceeds only slowly. We used the TEV protease and a highly specific cleavage site. The protease was appended to the C-terminus of the PDGFR transmembrane (TM) domain of ligand constructs (FIG. 1). The cleavage site was located between the cytoplasmic portion of the receptor and an artificial peptide transcription factor. After cleavage, the transcription factor is released and activates the expression of a reporter gene (FIG. 1). Critically, because the potential ligand and its receptor are both anchored in the plasma membrane, any interaction between them can cause approximation of the intracellular reactants to which they are appended and facilitate the generation of a signal.

In this system the effective molarity parameter operates at two levels. First, because the reactants are confined and co-localized in the plasma membrane there is a powerful effect of sequestration that favors interaction. Secondly, when these sequestered molecules interact they bring the enzyme and substrate components together, thereby greatly increasing the effective molarity of the signaling components of the system. It is important to note that this system only requires molecular interaction in the membrane and is largely independent of any specialized effects such as conformational changes resulting from the interaction.

Example 3. Concept Validation

To validate the method, we studied both single and multiple pass membrane proteins. For the single pass receptors, we studied the natural thrombopoietin (TPO) ligand as well as scFv antibodies generated previously by us to the thrombopoietin receptor (TpoR) (Zhang et al., *Chemistry & biology* 20:734-741, 2013). For the multiple pass membrane receptors, we studied the recognition of peptides by the GLP-1 GPCR receptor.

Figure 2:
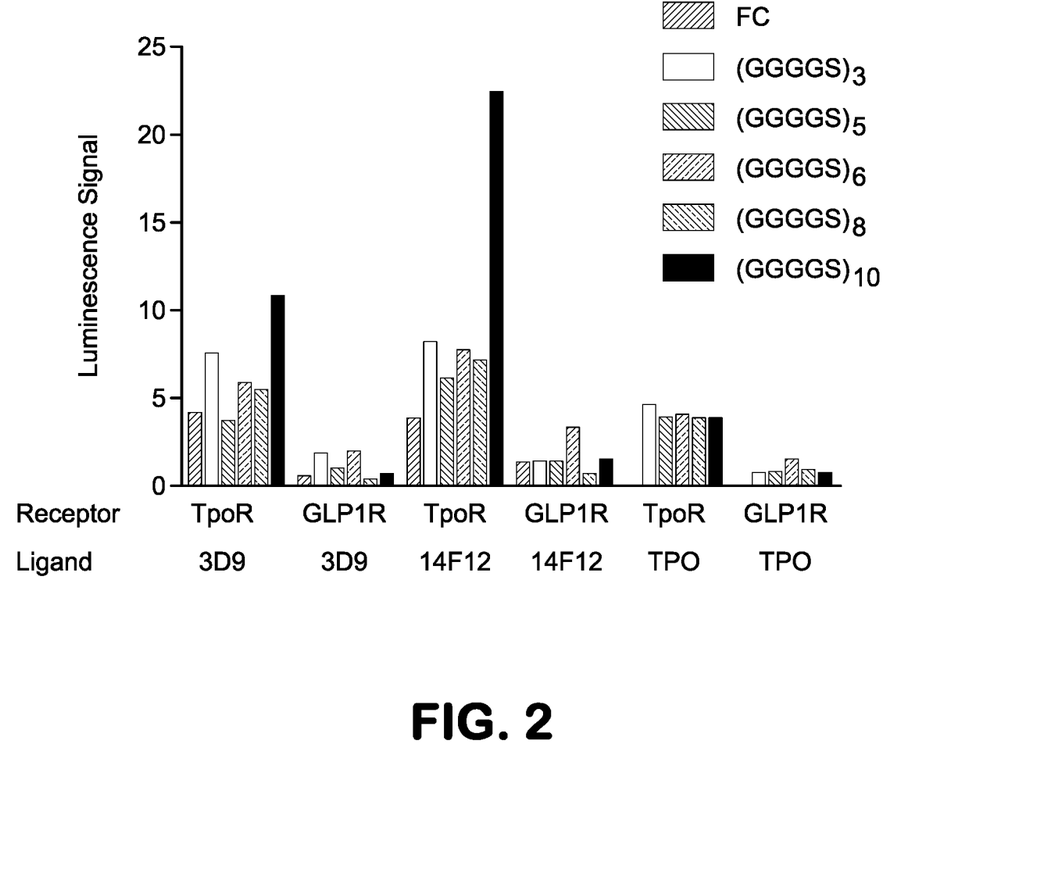

The hormone TPO or the TPOR binding antibodies, 3D9 or 14F12, were displayed on the cell surface by fusing them to the N-terminus of the PDGFR trans-membrane domain. A similarly constructed irrelevant antibody was used as a negative control. The membrane tethered 3D9-scFv protein can activate the TpoR sie-bla reporter cell line, and, thus, was used as a positive control. The antibodies or authentic TPO displayed at the plasma membrane increased the transcription factor mediated signal relative to the irrelevant antibody control (FIG. 2). We also carried out an orthogonal experiment to control for non-specific interactions of peptides or antibodies with the receptor component of the system. For this, we studied a cell line harboring the GLP1R-transcription factor fusion and irrelevant activators such as the TPO activating antibodies or TPO that were only active in the cells expressing the TPOR. The results showed that display of antibodies or TPO did not increase the signal in cells bearing the wrong receptor. We also tested the effect the length of the linker between the ligand and TM domain on proximity-based reactions. Thrombopoietin has 332 AA and an scFv has about 250 AA. TPO tethered to the plasma membrane by 3 to 9 tandem repeats of GGGGS (SEQ ID NO:1) generated similar signals while, in the case of the scFv, a longer distance resulted in higher activity (FIG. 2). Thus, the longer flexible linker may be of more general utility.

We next studied whether the method could be used for multiple pass membrane proteins. In a previous study, we found that membrane tethered Exendin-4 can activate the glucagon-like peptide-1 receptor (GLP1R). Thus, we used the GLP-1R and Exendin-4 as a receptor ligand pair for this study. The GLP1R belongs to the β 1 family of the seven-trans membrane G protein-coupled receptors. The binding model for a Class B receptor binding peptide ligand envisions a two-step mechanism where the C-terminal part of the peptide ligand interacts initially with the N-terminal ectodomain of the receptor. In the second step, the N-terminus of the ligand interacts with trans-membrane helices and connecting loops of the receptor, which leads to activation and signal transduction.

Figure 3A:
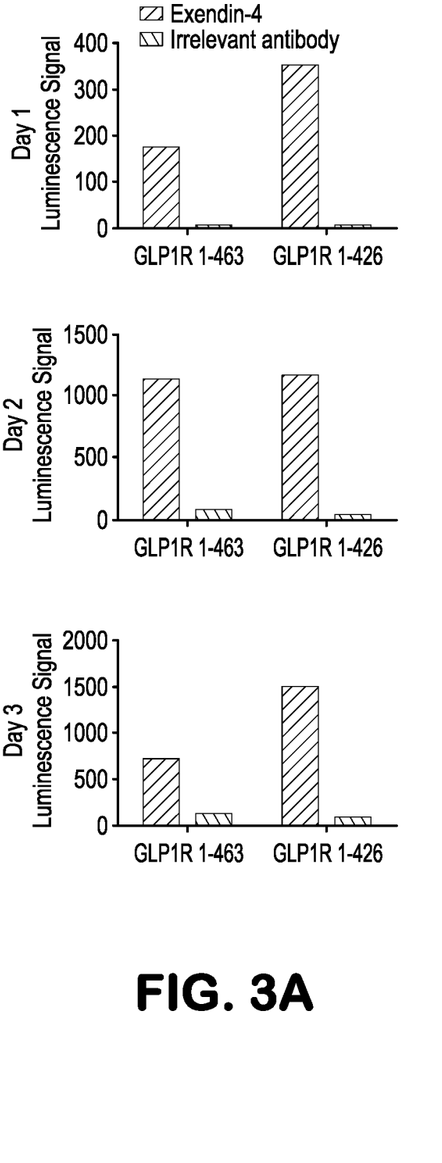
Figure 3B:
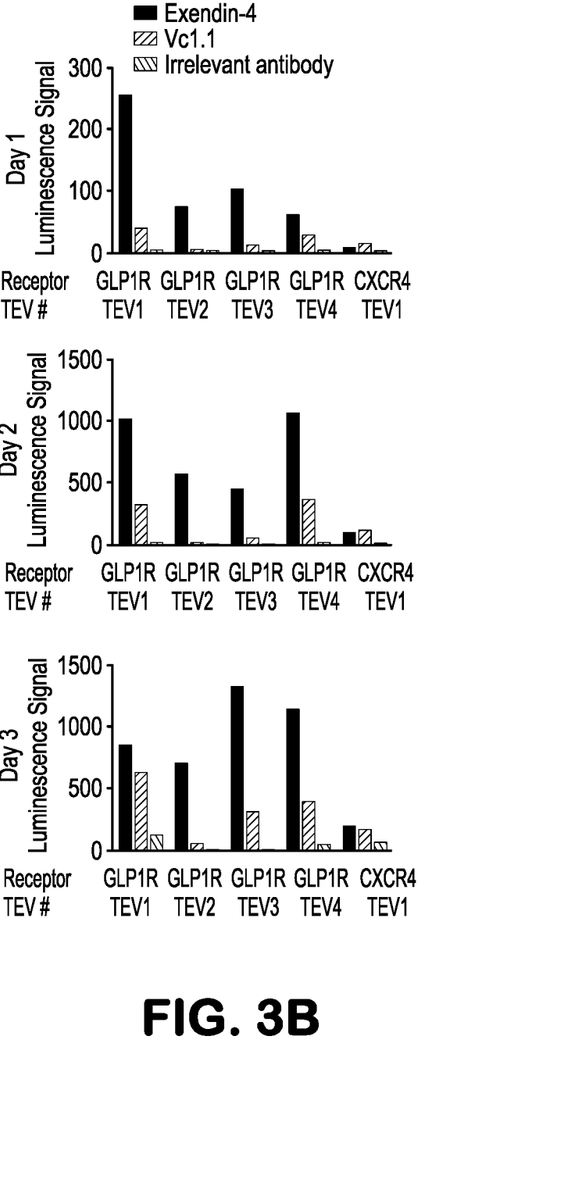

We fused the full length GLP1R to the transcription factor. The membrane tethered Exendin-4 was fused to the TEV protease at its C-terminal intracellular domain. The interaction of the co-expressed receptor and Exendin-4 resulted in significantly increased signal activity starting from day 1 that continued thru day 3 post infection (FIG. 3A). We also tested whether the length of the C-terminal tail of the GLP1R to which the transcription factor was appended had an effect on the signal to noise (S/N) ratio. The full-length receptor has a 59AA intracellular tail. Previous studies demonstrated that the C-terminus could be truncated as far as the C-terminal Leu422 residue without affecting GLP-1 potency or expression of the receptor. The intracellular tail of the truncated receptor has 22 amino acids. We fused amino acids 1-426 of the GLP1R to the releasable transcription factor that was appended to the truncated receptor. The construction with the shorter receptor intracellular tail generated a higher S/N ratio. As further controls, we studied non-specific peptide ligands of similar lengths. Non-specific peptides such as Vc1.1, which is blocker of the nAChR (nicotinicacetylcholine receptor)/GABA (metabotropic GABA receptor) resulted in an even lower S/N (FIG. 3B). Finally, no response was seen when the irrelevant G protein-coupled receptor, CXCR4, replaced the GLP1R (FIG. 3B).

Example 4. Effect of Different TEV Cleavage Sites

To reduce the noise while maintaining the strength of the signal, four TEV substrate sequences that can be cleaved by TEV with different efficiencies were tested. TEV protease recognizes a linear epitope of the general form E-X-X-Y-X-Q-G (SEQ ID NO:2) or E-X-X-Y-X-Q-S(SEQ ID NO:3), with cleavage occurring between Q and G or Q and S. The most efficient substrate was ENLYFQS (SEQ ID NO:4) (TEV1), which we had used in all the above experiments.

We hypothesized that substrate sequences that were less efficiently cleaved would generate less noise while maintaining the strength of the signal. A systematic study demonstrated that many different amino acids could be accommodated in different positions with different cleavage efficiencies (Kcat/Km). We compared the S/N ratio of four different sequences ENLYFQS (SEQ ID NO:4) (TEV1), ENFYFQS (SEQ ID NO:5) (TEV 2), ENLYYQS (SEQ ID NO:6) (TEV 3) and ENLFFQS (SEQ ID NO:7) (TEV 4). Their respective kcats/Km are 4.51±0.65; 0.024±0.001; 0.056±0.005; 0.35±0.041 mM$^{-1}$·s$^{-1}$.

We monitored the effect of employing these sequences on reaction kinetics in the proximity based signaling system. The relatively poor TEV2 substrate engendered the highest S/N ratio even after 3 days post infection while the better TEV1 and TEV4 substrates led to a very high level of noise starting from day 2 (FIG. 3B). Thus, TEV2 is, at present, the optimal cleavage site for control of the proximity enhanced reaction.

Example 5. Fluorescence Proteins can be Used as Reporter Genes

Figure 4:
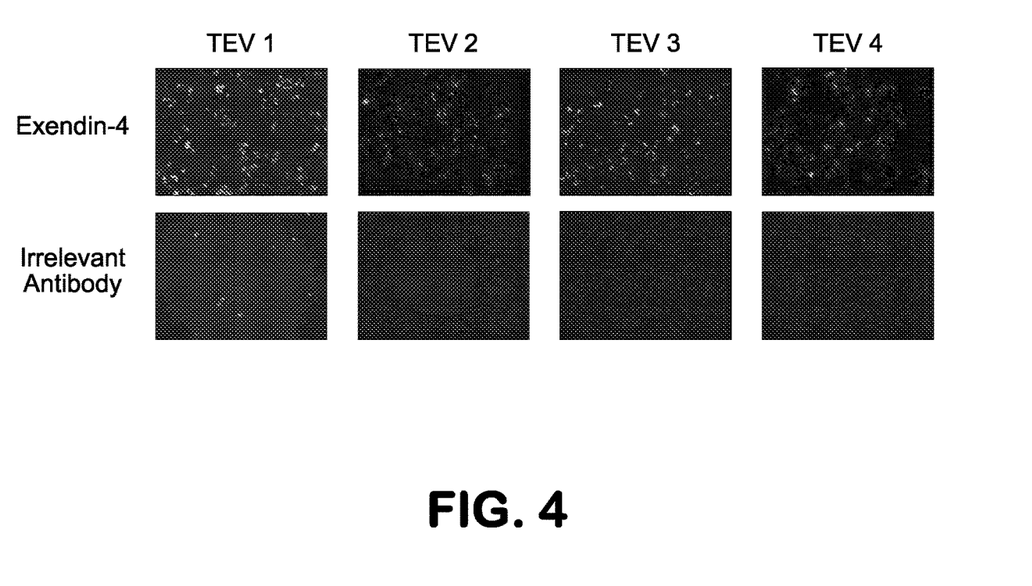

For the proximity based reaction to be used generally for selection of functional antibodies or peptides, reporter genes such as GFP or β lactamase can be ideal when coupled with a selection method such as fluorescence activated cell sorting. In addition, fluorescence proteins are useful for dynamic cell assays in living cells, enabling the assessment of a signaling activity over time in a single sample. As shown in FIG. 4, we used tdTomato as a reporter gene and observed its expression under the microscope. Consistent with the results using the luciferase reporter gene, membrane tethered Exendin-4 induced a high percentage of cells expressing tdTomato while an irrelevant protein (antibody) failed to generate appreciable amounts of fluorescence. Notably, weakened TEV2 and TEV3 cleavage sites exhibited much lower background.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, databases, GenBank sequences, patents, and patent applications cited in this specification are herein incorporated by reference as if each was specifically and individually indicated to be incorporated by reference.

We claim:

1. A method for identifying a binding partner that binds to a target polypeptide, comprising (a) generating a first construct expressing a first fusion molecule comprising the target polypeptide containing a first transmembrane domain (TM), and a second construct expressing a combinatorial library of second fusion molecules each comprising a candidate binding partner linked to a second transmembrane domain (TM), wherein one of the fusion molecules further comprises an enzyme, and the other fusion molecule further comprises a substrate sequence of the enzyme and an activator of an artificial signaling pathway, (b) expressing the first construct and the second construct in a host cell to generate a population of cells, wherein each cell has the first fusion molecule and a second fusion molecule co-localized to the plasma membrane, (c) selecting a cell from the population of cells in which the artificial signaling pathway is activated, and (d) identifying the second fusion molecule in the selected cell; thereby identifying a binding partner of the target polypeptide, wherein the target polypeptide is a cellular receptor, and the binding partner is a ligand of the receptor.

2. The method of claim 1, wherein the first transmembrane domain (TM) is a native domain of the target polypeptide.

3. The method of claim 1, wherein the first transmembrane domain (TM) is recombinantly fused to the target polypeptide.

4. The method of claim 1, wherein the enzyme is linked at its N-terminus to the second transmembrane domain, and the substrate sequence is linked at its N-terminus to the first transmembrane domain and at its C-terminus to the activator.

5. The method of claim 1, wherein cleavage of the substrate sequence by the enzyme results in release of the activator from the second fusion molecule.

6. The method of claim 1, wherein the cellular receptor is a cell surface receptor, and the second transmembrane domain is a PDGFR transmembrane domain.

7. The method of claim 1, wherein the cellular receptor is a G-protein coupled receptor (GPCR).

8. The method of claim 1, wherein the cellular receptor is TpoR or GLP1R.

9. The method of claim 1, wherein the enzyme is a protease, and the substrate sequence comprises a cleavage site of the protease.

10. The method of claim 9, wherein the protease is TEV protease.

11. The method of claim 10, wherein the substrate sequence comprises ENLYFQS (SEQ ID NO:4) (TEV 1), ENFYFQS (SEQ ID NO:5) (TEV 2), ENLYYQS (SEQ ID NO:6) (TEV 3), or ENLFFQS (SEQ ID NO:7) (TEV 4).

12. The method of claim 1, wherein the candidate binding partner is a peptide or an antibody.

13. The method of claim 1, wherein the candidate binding partner is linked to the second transmembrane domain via a linker sequence.

14. The method of claim 13, wherein the linker sequence comprises 3, 5, 6, 8, 10, or more tandem repeats of GGGGS (SEQ ID NO:1).

15. The method of claim 1, wherein the activator is a transcription factor, and the artificial signaling pathway is expression of a reporter gene under the control of a transcription regulatory sequence recognized by the transcription factor.

16. The method of claim 15, wherein the reporter gene is introduced into the host cell via a lentiviral vector.

17. The method of claim 15, wherein the reporter gene is introduced into the host cell prior to expression of the fusion molecules.

18. The method of claim 15, wherein the transcription factor is GAL4-V16, and the transcription regulatory sequence comprises GAL4 UAS and the adenovirus late promoter.

19. The method of claim 15, wherein the reporter gene is luciferase luc2P gene or tdTomato reporter gene.

20. The method of claim 1, wherein the host cell is HEK293 or HEK293T cell.

21. The method of claim 1, wherein the host cell stably expresses the first fusion molecule.

22. The method of claim 21, wherein the second fusion molecule is expressed in the host cell via a lentiviral vector.

* * * * *